US00PP26027P3

(12) United States Plant Patent
Suphachadiwong

(10) Patent No.: US PP26,027 P3
(45) Date of Patent: Oct. 27, 2015

(54) *DISCHIDIA* PLANT NAMED 'IDEAMINUBU'

(50) Latin Name: *Dischidia nummularia*
Varietal Denomination: IDEAMINUBU

(71) Applicant: Thumrong Suphachadiwong, Chonburi (TH)

(72) Inventor: Thumrong Suphachadiwong, Chonburi (TH)

(73) Assignee: Plants and Ideas, Bangkok (TL)

( * ) Notice: Subject to any disclaimer, the term of this patent is extended or adjusted under 35 U.S.C. 154(b) by 23 days.

(21) Appl. No.: 13/986,856

(22) Filed: Jun. 11, 2013

(65) Prior Publication Data

US 2014/0366235 P1 Dec. 11, 2014

(51) Int. Cl.
*A01H 5/00* (2006.01)

(52) U.S. Cl.
USPC ..... Plt./373

(58) Field of Classification Search
USPC ..... Plt./263.1, 226, 373
See application file for complete search history.

*Primary Examiner* — Keith O. Robinson

(57) ABSTRACT

A new and distinct *Dischidia* cultivar named 'IDEAMINUBU' is disclosed, characterized by strongly convexed, orbicularly shaped green leaves The new variety is a *Dischidia*, typically produced as an indoor or outdoor ornamental plant.

1 Drawing Sheet

Latin name of the genus and species: *Dischidia nummularia.*

Variety denomination: 'IDEAMINUBU'.

BACKGROUND OF THE INVENTION

The new cultivar is the product of chance discovery. The new variety originated as a naturally occurring whole plant mutation of an unpatented, unnamed variety of *Dischidia nummularia.*

The new variety was discovered by the inventor, Thumrong Suphachadiwong, a citizen of Thailand, during 2004 in a commercial greenhouse belonging to the inventor in Chonburi, Thailand. After identifying the new variety as a potentially interesting selection, the inventor continued confidential testing and propagation of 'IDEAMINUBU' assessing stability of the unique characteristics of this variety.

Asexual reproduction of the new cultivar 'IDEAMINUBU' was first performed by cuttings during 2004 in a commercial greenhouse belonging to the inventor in Chonburi, Thailand. Access to all plants was restricted, as plants were kept in a location that is not open to the public. Through subsequent propagation by cuttings, multiple generations have been reproduced, which have shown that the unique features of this cultivar are stable and reproduced true to type.

SUMMARY OF THE INVENTION

The cultivar 'IDEAMINUBU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IDEAMINUBU.' These characteristics in combination distinguish 'IDEAMINUBU' as a new and distinct *Dischidia* cultivar:

1. Orbicular shaped leaves.
2. Strongly convex leaves
3. Medium green foliage.

4. Suitability for market use as an indoor or outdoor foliage plant in a container, for decorative purposes only.

PARENT COMPARISON

Plants of the new cultivar 'IDEAMINUBU' are similar to the unpatented, unnamed parent, *Dischidia nummularia* in most horticultural characteristics. The new variety, however, produces leaves that are darker green and smaller than those of the parent. Foliage arrangement of the new variety is different, and much more closely spaced than the parent variety. Additionally the leaf shape of the new variety is different than the parent.

COMMERCIAL COMPARISON

Plants of the new cultivar 'IDEAMINUBU' are similar to the commercial variety *Dischidia* 'Supha08' U.S. Plant Pat. No. 21,202, in most horticultural characteristics. The new variety, however, produces larger, lighter colored leaves. 'IDEAMINUBU' also produces foliage in a different arrangement than 'Supha08'.

BRIEF DESCRIPTION OF THE PHOTOGRAPH

The accompanying photograph in FIG. 1 illustrates in full color a typical plant of 'IDEAMINUBU' grown in a commercial greenhouse in Honselersdijk, Netherlands. This plant is approximately 8 to 9 months old, shown planted in a 10 cm. container.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'IDEAMINUBU' plants grown in a greenhouse in Honselersdijk, Netherlands. The plants are about 8 to 9 months old from the planting of a rooted cutting in a 10 cm. pot. The growing temperature ranged from 20° C. to 22° C. during the day and from 20° C. to 21° C. during the night. General light conditions are bright, normal sunlight. Measurements and numerical values represent averages of typical plant types.

Botanical classification: *Dischidia nummularia* 'IDEAMINUBU'.

Propagation:

*Typical propagation method*.—Cuttings.

*Time to initiate rooting*.—About 1 week at approximately 20° C.

*Time to produce a rooted cutting*.—4-5 weeks.

*Root description*.—Thin, moderately dense, non-fleshy, very slightly fibrous, coloured greyed-yellow; Greyed-Yellow near RHS 161C and 161D.

*Aerial root description*.—Average length: 1.4 cm, average width: 0.05 cm, coloured yellow-green, near RHS 148B and 148C.

Plant:

*Growth habit*.—Prostrate to spreading.

*Height*.—Approximately 7.5 cm.

*Plant spread*.—Approximately 17.7 cm.

*Growth rate*.—Moderate, approximately 2 cm per month.

*Branching characteristics*.—

*Main stem*.—No main stems present. Lateral stems grow directly from the base/roots.

*Lateral stem*.—Quantity: Average 17. Diameter: Approximately 0.2 cm. Length: Approximately 9.7 cm. Texture: Smooth, slightly glossy. Color: Green; near RHS 139A and 143A. Strength: Strong. Number of leaves per stem: Average: 78 (39 pairs).

*Internode length*.—Average 0.25 cm.

Foliage:

*Leaf*.—Arrangement: Opposite. Average length: Approximately 0.8 cm. Average width: Approximately 0.85 cm. Shape of blade: Orbicular. Aspect: Strongly convexed. Angle of Attachment: Average angle: 45°. Type of Attachment: Petiolate. Apex: Retuse. Base: Short attenuate. Margin: Entire. Texture of top surface: Smooth, moderately glossy. Texture of bottom surface: Smooth, moderately glossy. Color: Young foliage upper side: Yellow-green; near RHS 144A. Young foliage under side: Yellow-green; near RHS 144A. Mature foliage upper side: Green to yellow-green; in between near RHS 143B and 144A. Mature foliage under side: Yellow-green; near RHS 148C. Venation: Type: No veins visible.

*Petiole*.—Average length of petiole: 0.15 cm, average width of petiole: 0.1 cm, upper side of petiole colored green to yellow-green; in between near RHS 143B and 144A, under side of petiole colored yellow-green; near RHS 148C.

*Other distinguishing characteristics*.—Foliage produces a milky sap colored white, near RHS NN155D. Stipules, tendrils, thorns, and spines are not produced by the new variety. Flowering has not been observed in this variety.

Other characteristics:

*Disease resistance*.—Neither resistance nor susceptibility to normal diseases and pests of *Dischidia* observed to date. Diseases can include powdery mildew, or other diseases commonly found in moist environments. Pests can include aphids.

*Drought tolerance*.—Will tolerate considerable dryness once established.

*Temperature tolerance range*.—Lowest temperature tolerance is unknown, indoor variety, at least hardy to USDA Zone 10; max temperature tolerance is unknown but at least tolerant to temperatures up to 40° C.

*Fruit/seed production*.—Not observed to date.

What is claimed is:

1. A new and distinct cultivar of *Dischidia* plant named 'IDEAMINUBU' as herein illustrated and described.

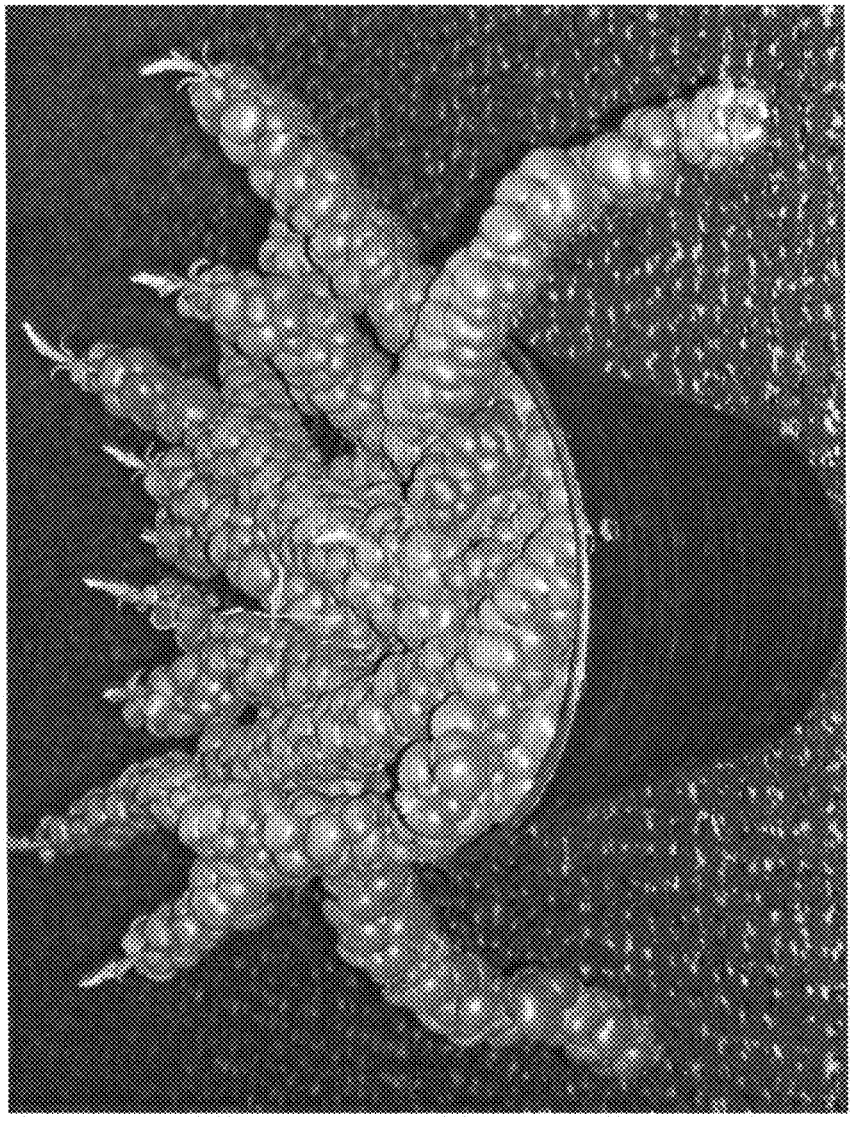

* * * * *